United States Patent
Adoni et al.

(10) Patent No.: US 11,841,557 B2
(45) Date of Patent: Dec. 12, 2023

(54) SMART CONTACTS THAT RESPOND TO FLUID CHANGES ON THE SURFACE OF THE EYES

(71) Applicant: International Business Machines Corporation, Armonk, NY (US)

(72) Inventors: Siddique M. Adoni, St. Thomas Town (IN); Sarbajit K. Rakshit, Kolkata (IN)

(73) Assignee: International Business Machines Corporation, Armonk, NY (US)

( * ) Notice: Subject to any disclaimer, the term of this patent is extended or adjusted under 35 U.S.C. 154(b) by 324 days.

(21) Appl. No.: 17/307,021

(22) Filed: May 4, 2021

(65) Prior Publication Data

US 2022/0357592 A1 Nov. 10, 2022

(51) Int. Cl.
G02C 7/04 (2006.01)
A61B 5/00 (2006.01)
G02C 11/00 (2006.01)

(52) U.S. Cl.
CPC ............ *G02C 7/049* (2013.01); *A61B 5/4875* (2013.01); *A61B 5/6821* (2013.01); *G02C 11/10* (2013.01);
(Continued)

(58) Field of Classification Search
CPC .......... G02C 7/049; G02C 11/10; G02C 7/04; A61B 5/4875; A61B 5/6821;
(Continued)

(56) References Cited

U.S. PATENT DOCUMENTS 8,864,306 B2  10/2014 Juan, Jr.
9,086,580 B2   7/2015 Grant
(Continued)

FOREIGN PATENT DOCUMENTS

EP   3619570 A1   3/2020

OTHER PUBLICATIONS

"Far Point And Near Point Vision Diagram", Anatomy Note, Sep. 21, 2019, 4 pages, <https://www.anatomynote.com/human-anatomy/ophthalmology-eye-anatomy/far-point-and-near-point-vision-diagram/>.
(Continued)

*Primary Examiner* — Balram T Parbadia
*Assistant Examiner* — Gabriel A Sanz
(74) *Attorney, Agent, or Firm* — Edward J. Wixted, III

(57) ABSTRACT

An apparatus, worn over the eyes of a user, that restores visual clarity to the user in response to a change associated with a film of fluid over the apparatus. In an embodiment the apparatus includes a smart contact portion having at least a first convex surface, a second convex surface, and a concave surface. The apparatus further includes set of liquid thickness sensors embedded upon the first convex surface. The apparatus further includes an electrochemical storage device and a computing module. The apparatus further includes a plurality of ultrasonic transducers embedded upon the first convex surface. The apparatus further includes an electroactive lens structure embedded within central portion of the first convex surface. The apparatus further includes lens controllers that apply electrical signals to the electroactive lens structure to change at least one physical characteristic of the electroactive lens structure based on control signals from the computing module.

15 Claims, 5 Drawing Sheets

(52) U.S. Cl.
CPC . *A61B 2560/0214* (2013.01); *A61B 2562/046* (2013.01)

(58) Field of Classification Search
CPC ...... A61B 2560/0214; A61B 2562/046; A61B 2562/164; A61B 5/002; A61B 5/1075; A61B 2562/029; A61B 2562/12
See application file for complete search history.

(56) References Cited

U.S. PATENT DOCUMENTS

| | | | |
|---|---|---|---|
| 2001/0050750 A1 | 12/2001 | Breger | |
| 2012/0140167 A1* | 6/2012 | Blum | G02C 7/04 351/159.73 |
| 2013/0245754 A1* | 9/2013 | Blum | A61F 2/1635 623/6.22 |
| 2016/0299354 A1 | 10/2016 | Shtukater | |
| 2017/0068119 A1 | 3/2017 | Antaki | |
| 2018/0004012 A1* | 1/2018 | Pugh | G02F 1/29 |
| 2018/0246049 A1* | 8/2018 | Gutierrez | G02C 11/10 |
| 2019/0282399 A1* | 9/2019 | Goetz | A61B 8/54 |
| 2020/0310163 A1* | 10/2020 | Zheng | G02C 7/04 |
| 2020/0333630 A1* | 10/2020 | Toner | G02C 7/04 |
| 2020/0337552 A1* | 10/2020 | Wang | A61B 3/101 |

OTHER PUBLICATIONS

"Laser Surgery Can Improve Vision Problems", University of Rochester Medical Center, Printed Apr. 22, 2021, 7 pages, <https://www.urmc.rochester.edu/encyclopedia/content.aspx?contenttypeid=1&contentid=2052>.

"Smart graphene contact lenses bring wearable electronics to the eye", Nanowerk, May 22, 2017, 5 pages, <https://www.nanowerk.com/spotlight/spotid=46780.php>.

"The Magnifying Effect of a Water Drop", Scientific American, Jul. 2, 2015, 9 pages, <https://www.scientificamerican.com/article/the-magnifying-effect-of-a-water-drop/>.

"Ultrasonic thickness measurement", Wikipedia, last edited on Sep. 21, 2020, 4 pages, <https://en.wikipedia.org/wiki/Ultrasonic_thickness_measurement>.

Ali et al., "Google Smart Contact Lens Monitoring Diabetes from Tears", IJESC, vol. 6 Issue No. 3, Mar. 2016, 5 pages, <http://ijesc.org/>.

Boyd, Kierstan, "Contact Lenses for Vision Correction", American Academy of Ophthalmology, Mar. 4, 2021, 5 pages, <https://www.aao.org/eye-health/glasses-contacts/contact-lens-102>.

Choi et al., "Smart Reinvention of the Contact Lens with Graphene", ACS Nano, Printed May 3, 2021, 4 pages.

Elgan, Mike, "Why a smart contact lens is the ultimate wearable", ComputerWorld, May 9, 2016, 6 pages, <https://www.computerworld.com/article/3066870/why-a-smart-contact-lens-is-the-ultimate-wearable.html>.

Gorey, Colm, "Smart contact lenses harness tears to prevent dry eyes", Siliconrepublic, Jan. 23, 2020, 22 pages, <https://www.siliconrepublic.com/machines/contact-lenses-non-dry>.

Jacobs, Suzanne, "What Else Could Smart Contact Lenses Do?", MIT Technology Review, Jul. 22, 2014, 8 pages <https://www.technologyreview.com/2014/07/22/171 1982/what-else-could-smart-contact-lenses-do/>.

Kusama et al., "Self-Moisturizing Smart Contact Lens Employing Electroosmosis", Advanced Materials Technology, 2019, 9 pages.

McIntosh, James, "Causes and treatments for watering eyes", Medical News Today, Feb. 23, 2017, 8 pages, <https://www.medicalnewstoday.com/articles/169397#_noHeaderPrefixedContent>.

Mukamal, Reena, "High-Tech Contact Lenses That Go Beyond Correcting Vision", American Academy of Ophthalmology, Feb. 5, 2020, 5 pages, <https://www.aao.org/eye-health/tips-prevention/smart-contact-lens-tech-beyond-vision-correction>.

Refojo, Miguel, F., "Tear Evaporation Considerations and Contact Lens Wear", National Center for Biotechnology Information Bookshelf, A service of the National Library of Medicine, National Institutes of Health, 1991, 5 pages, <https://www.ncbi.nlm.nih.gov/books/NBK234103/>.

* cited by examiner

SMART CONTACTS THAT RESPOND TO FLUID CHANGES ON THE SURFACE OF THE EYES

BACKGROUND OF THE INVENTION

The present invention relates generally to the field of wearable device technology, and more particularly to smart contact lenses capable of maintaining visual clarity for a wearer in response to changes to fluid on the surface of the eyes of the wearer.

Smart contact lenses are available today that correct color blindness, that seamlessly transition from light to dark environments, that correct myopia or nearsightedness, and even smart contact lenses that slow the progression of nearsightedness in children. Typically, smart contact lenses consist of a pair of soft contact lenses with a number of very thin, biocompatible electronic devices and sensors. A number of different methods to power smart contact lenses are under development including very thin batteries, solar cells, and using a wearable power source, such as a battery powered wrist band to wirelessly or optically power or recharge the smart contact lenses of a user.

In addition, smart contacts can be linked to other wearable devices and/or mobile devices, such as smart watches, mobile phones, tablet computers, etc. Linking the smart contacts to another electronic device can provide additional computational power that the smart contact lacks, enables monitoring and storage of information related to the wearer of the smart contacts, aids in determining contextual information associated with the wearer and environment condition in proximity to the wearer, etc.

SUMMARY

According to an aspect of the present invention, there is an apparatus for restoring visual clarity to a user in response to a change associated with a film of fluid over the apparatus. In an embodiment, the apparatus includes a smart contact portion having at least a first convex surface, a second convex surface, and a concave surface. The apparatus further includes set of liquid thickness sensors embedded upon the first convex surface. The apparatus further includes an electrochemical storage device and a computing module. The apparatus further includes a plurality of ultrasonic transducers embedded upon the first convex surface. The apparatus further includes an electroactive lens structure embedded within central portion of the first convex surface. The apparatus further includes lens controllers that apply electrical signals to the electroactive lens structure to change at least one physical characteristic of the electroactive lens structure based on control signals from the computing module.

According to another aspect of the present invention, there is computer-implemented method to maintain visual clarity of a user wearing a smart contact in response to a change associated with a film of fluid over the smart contact. In an embodiment, the computer-implemented method includes a computing module determining that a thickness value associated with a film of fluid over a smart contact worn on an eye of a user differs more than a threshold value. The computer-implemented method further includes determining, utilizing a double lens system calculation, a change to the shape of an electroactive lens structure included within the smart contact based on the determined thickness value associated with the film of fluid over the smart contact and one or more physical characteristic of the electroactive lens structure. The computer-implemented method further includes determining a first set of control values based on the calculated change to the shape of the electroactive lens structure of the smart contact. The computer-implemented method further includes applying the first set of control values among a set of controllers operatively coupled to the electroactive lens structure that produce electrical signals, which modify at least a curvature characteristic of the electroactive lens structure.

DETAILED DESCRIPTION

Figure 1:
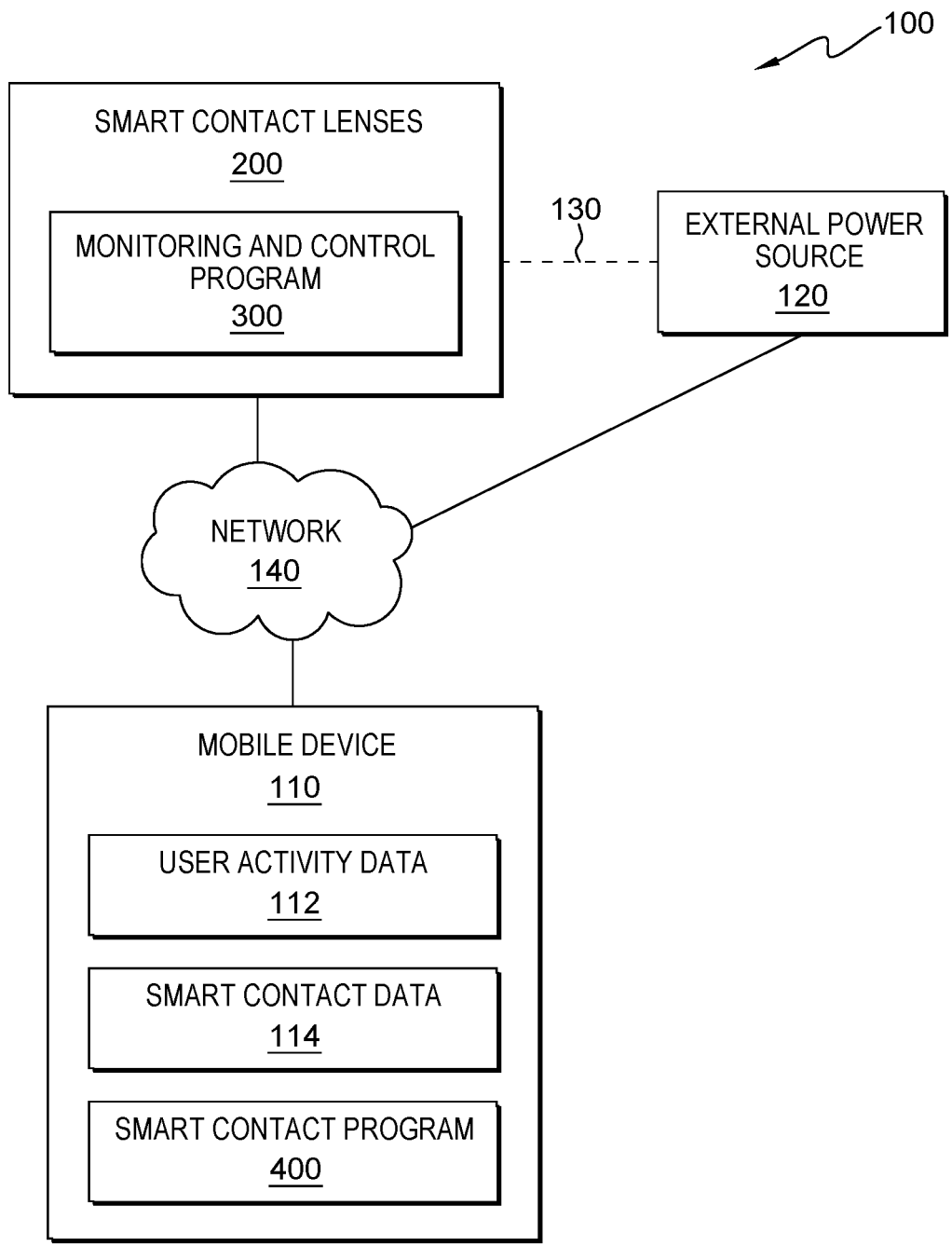
FIG. 1 illustrates a networked environment, in accordance with an embodiment of the present invention.

Embodiments of the present invention recognize that additional transparent fluid films or liquid droplets on the exterior surface of the lens area of an eye causes blurred vision for an individual by changing the focal length of the lens of the eye and/or creating localized distortions. For example, an accumulation of tears in the eye(s) of the individual can cause temporary blurred vision. Embodiments of the present invention recognize that tears can be generated by the eye(s) of the individual because of an eye problem, such as a medical condition; a change in emotional state of the individual (e.g., laughing, sadness, joy, anger); and/or environmental factors, such as strong wind in the face, dust, pollen, fumes, and other irritants. Embodiments of the present invention also recognize that other clear liquids, such as raindrops, water from washing, eye drops, backsplash of a liquid, sweat, etc., can deposit the surface of the eyes of an individual that temporarily blurs the vision of the individual.

Embodiments of the present invention also recognize that some individuals wear contact lenses to correct the vision of the user and that the contact lens material may have surface tension characteristics different from the eye of the individual, which can affect the uniformity of the additional fluid on the surface of the eye(s) of the individual. For example, contact lenses may change the dispersal of the additional fluid in the eyes of the individual, increasing the duration of the blurred vision for the individual. Embodiments of the present invention further recognize that blurred vision can adversely affect the safety of the individual and/or impact tasks performed by the individual. In addition, embodiments of the present invention recognize that some individuals wear smart contact lenses that enable a user to utilize and/or interface with technologies, such as gaze tracking, security measures, virtual interfaces, etc.

Embodiments of the present invention describe an apparatus (i.e., smart contact lenses) and a method for controlling the apparatus that automatically restores clear vision to an individual in response to detecting the presence of additional fluid, a film or droplets on the surface of the lens area of a smart contact over the pupil of the eye(s) of an individual (i.e., user). As used herein, smart contacts and smart contact lenses can be used interchangeably. Embodiments of the present invention activate a plurality of ultrasonic transducers included within or on the smart contact lenses in response to detecting a change to thickness and/or uniformity of fluid approaching or over given/dictates perimeter (i.e., area) that includes the lens portion of the smart contacts worn by the user over one or both eyes. Embodiments of the present invention control the plurality of ultrasonic transduces produce a uniform fluid film thickness (e.g., level out thickness irregularities) over the area that includes the lens portion of the smart contacts and determine the thickness and/or index of refraction of the film of fluid on the surface of the eye(s) of the user. In response to generating a uniform film/fluid thickness, embodiments of the present invention subsequently apply electrical signals to one or more electroactive materials of the lens portion of the smart contacts to adjust the focal length of the lens of the smart contacts based on performing double lens (e.g., two lens) system calculations to compensate for the change to the thickness and/or index of refraction of fluid film over the at least the lens portion of the smart contacts worn the user.

Embodiments of the present invention utilize one or more other devices in the possession of the user to augment aspects of the smart contacts, such as performing additional computational tasks, storing information relate to the smart contacts and/or the user, supplying external power, rechanging the smart contacts, etc. Embodiments of the present invention can also utilize one or the other devices of the user, such as a smart phone or a wearable device to determine contextual and/or environmental information related to occurrences of additional fluid on the surface of the eyes of the user. The contextual and/or environmental information related to occurrences of additional fluid on the surface of the eyes of the user is analyzed utilizing machine learning (ML) or other cognitive techniques to determine the cause or situation associated with the additional fluid on the eyes of the user. Another embodiment of the present invention pre-emptively responds to detecting a cause or situation that previously produced an occurrence of blurred vision the eye(s) of the user to mitigate the effect to the vision of the user.

Embodiments of the present invention utilize other sensors and/or a mobile device of the user to obtain cues or other information from the user, such as a verbal acknowledgment that indicate whether or not an adjustment to the smart contacts restores clear vision to the user. Some embodiments of the present invention can correct the vision of a user in response to complete immersion of the eyes of the user of the smart contact within a fluid, such as while the user swims or in response the user losing a facemask while swimming. Further embodiments of the present invention can be incorporated within other devices with exposed lenses, such as trail cams, traffic monitors, or video equipment that are exposed to conditions where fluid and/or liquid droplets can adhere to lens and distort the imagery captured by the other devices.

The descriptions of the various scenarios, instances, and examples related to the present invention have been presented for purposes of illustration but are not intended to be exhaustive or limited to the embodiments disclosed.

The present invention will now be described in detail with reference to the Figures. FIG. 1 is a functional block diagram illustrating networked environment 100, in accordance with embodiments of the present invention. In one embodiment, networked environment 100 includes mobile device 110, external power source 120, and smart contact lenses 200 (e.g., one or more smart contacts) all interconnected over network 140. Networked environment 100 also includes a user (not shown) that wears an instance of smart contact lenses 200 on one or both eyes. In some embodiments, networked environment 100 also includes more than one instance of external power source 120 and power transmission link 130. Mobile device 110 and/or external power source 120 may be worn by the user or be within a proximity of the user.

Mobile device 110 may be a laptop computer, a tablet computer, a personal computer, or any programmable computer systems known in the art. In certain embodiments, mobile device 110 represents a computer system utilizing clustered computers and components (e.g., database server computers, application server computers, etc.) that act as a single pool of seamless resources when accessed through network 140, as is common in data centers and with cloud-computing applications. In some embodiments, mobile device 110 can be a personal digital assistant (PDA), a smart phone, a wearable device (e.g., smart glasses, a smart watch, e-textiles, an AR headset). In general, mobile device 110 is representative of any programmable electronic device or combination of programmable electronic devices capable of executing machine readable program instructions and communicating via network 140 with at least smart contact lenses 200. Mobile device 110 may include components, as depicted and described in further detail with respect to FIG. 5, in accordance with embodiments of the present invention.

Mobile device 110 includes user activity data 112, smart contact data 114, smart contact program 400, and a plurality of other programs and data (not shown). Examples of other programs and data included in mobile device 110 may include one or more databases, communication programs, cognitive programs, a web browser, a calendar function, a machine learning (ML) program, programs related to one or more other hardware features, etc. In some embodiments, mobile device 110 can also utilize network 140 to access the Internet or a cloud-service provider that stores control data parameters and respective responses (e.g., curvature/focal length changes) for various types and constructions of electroactive lenses.

In various embodiments, mobile device 110 also includes and/or is operatively coupled to one or more other hardware features or elements (not shown), such as a camera; a microphone; environmental sensors; a compass; and/or an inertial monitoring system to sense a position, orientation and/or one or more physical actions of the user; a global positioning system (GPS); wireless communication technologies and protocols, such as LTE-M, narrowband IoT (NB-IoT), near field communication (NFC), etc.

User activity data 112 includes a plurality of information respectively associated with previous occurrences of additional fluid upon the surface of an area of smart contacts lenses 200 that affected the clarity of the vision in one or both eyes of the user (not shown) while wearing smart contact lenses 200. Some information included within user activity data 112 is based on information gathered and sent to mobile device 110 by monitoring and control program 300 from smart contact lenses 200. Other information included within user activity data 112 is based on information obtained by one or more elements and/or features of mobile device 110, such as environmental data; physical data (e.g., user location, user movements). In various embodiments, user activity data 112 also includes contextual data determined or inferred by a cognitive program, such as identifying an activity that the user was performing, inferring a change to an emotional state of the user, etc. In some embodiments, user activity data 112 also include ophthalmic data associated with vision correction by smart contact lenses 200 for a type or group of activities that occur at differing distances (e.g., close, near, intermediate, and long ranges), such as reading, cooking, playing a sport, bird-watching, etc.

Smart contact data 114 may include lists, associative arrays, tables, or other data structures that can store interrelated information associated with occurrences of changes to a thickness of a fluid over an area that includes the lens portion of one or both instances of smart contact lenses 200 that the user is wearing. Smart contact data 114 may include data values and control parameters related to current and previous (i.e., historic) occurrences of blurry, distorted, and/or out-of-focus vision of the user. The vision changes are related to a change to a thickness, uniformity, and/or index of refraction of a film of fluid or droplets of fluid upon at least the lens portion of a smart contact of smart contact lenses 200 while a user is wearing an instance of a smart contact upon one or both eyes. For example, smart contact data 114 includes values corresponding to a fluid thickness, an index of refraction values corresponding to a fluid upon the surface of one or more eyes of the user; a power level, frequency, and/or duration applied via monitoring and control program 300 to a feature of smart contact lenses 200 to produce a uniform film thickness; control parameter values utilized to produce a given curvature and/or change of a shape of one or more portions of the lens portion of smart contact lenses 200, etc.

Smart contact program 400 is a program that analyzes data and information received from monitoring and control program 300 executing within each smart contact of smart contact lenses 200. Smart contact program 400 can control each smart contact of smart contact lenses 200 independently. In response, smart contact program 400 generates control data that is utilized by monitoring and control program 300 to activate and/or control various features of a smart contact to produce a uniform thickness of a film of fluid and improve the clarity of the vision of the user wearing smart contact lenses 200 by modifying the curvature of the lens portion of the smart contact. In some embodiments, smart contact program 400 utilizes one or more programs of mobile device 110 and information received from at least one smart contact of smart contact lenses 200 to determine contextual information related to an occurrence of the additional fluid upon a smart contact, such as determining why the eyes of the user are producing tears.

Various embodiments of the present invention can utilize various accessible data sources, such as user activity data 112, which may include storage devices and content associated with the user. In an example embodiment, monitoring and control program 300 and/or smart contact program 400 allow the user to opt-in or opt-out of exposing types and categories of information. A feature (not shown) of smart contact program 400 enables the authorized and secure handling of user information, such as location information, as well as types and categories of information that may have been obtained, is maintained, and/or is accessible. In addition, smart contact program 400 can control storage and utilization of data and information obtained from control and monitoring program 300 executing within smart contact lenses 200. In another example embodiment, a user opts-out of allowing smart contact program 400 to log contextual information related to the perceived emotional state of the user while wearing smart contact lenses 200. The user can be provided with notice of the collection of types and categories of information and the opportunity to opt-in or opt-out of the collection process. Consent can take several forms. Opt-in consent can impose on the user to take an affirmative action before the data is collected. Alternatively, opt-out consent can impose on the user to take an affirmative action to prevent the collection of data before that data is collected.

External power source 120 represents one or more power sources that recharge and/or supply additional operating power to smart contact lenses 200 via power transmission link 130. Power transmission link 130 represents a wireless transfer of power from external power source 120 to smart contact lenses 200. In some embodiments, external power source 120 receives information or commands via network 140 from smart contact lenses 200 and/or user device 110 to activate to provide power to smart contact lenses 200 via power transmission link 130.

In one embodiment, external power source 120 represents a photonic source of power that is converted to electrical energy by one aspect of smart contact lenses 200, such as a photodiode or an organic photocell. In one example, external power source 120 represents natural light and/or ambient illumination. In another example, external power source 120 represents an artificial light source that does not affect the vision of the user, such as infra-red LEDs. External power source 120 may be included within an item of apparel, such under the brim of a hat and directed towards the eyes of the user; or as a feature of a wearable device, such as smart glassed or an augmented reality headset. External power source 120 may include components, as depicted and described in further detail with respect to FIG. 5, in accordance with embodiments of the present invention.

In another embodiment, external power source 120 represents a source of transmitted electromagnetic energy, such as radio waves or microwaves that are converted to electrical energy by other aspects (e.g., features and/or functions) smart contact lenses 200. For example, power transmission link 130 may represent an inductive or beamed transfer of electromagnetic energy from external power source 120 to one or more smart contacts of smart contacts lenses 200.

Smart contact lenses 200 are electro-mechanical optical devices (i.e., smart contacts) worn on one or both eyes of a user to perform various functions, such as correct the vision of the user or provide other functions in addition to restoring clear vision to a user in response to a change to fluid on the surface of the eye(s) of the user. In various embodiments, smart contact lenses 200 wirelessly communicate with mobile device 110 and/or external power source 120 via network 140. For example, smart contact lenses 200 includes wireless communication technologies and protocols, such as LTE-M, narrowband IoT (NB-IoT), near field communication (NFC), etc. In a further embodiment, various aspects smart contact lenses 200 are incorporated within one or more of smart contacts that provide the user with other capabilities, such as gaze tracking, security measures, virtual interfaces, virtual displays, etc.

Figure 2A:
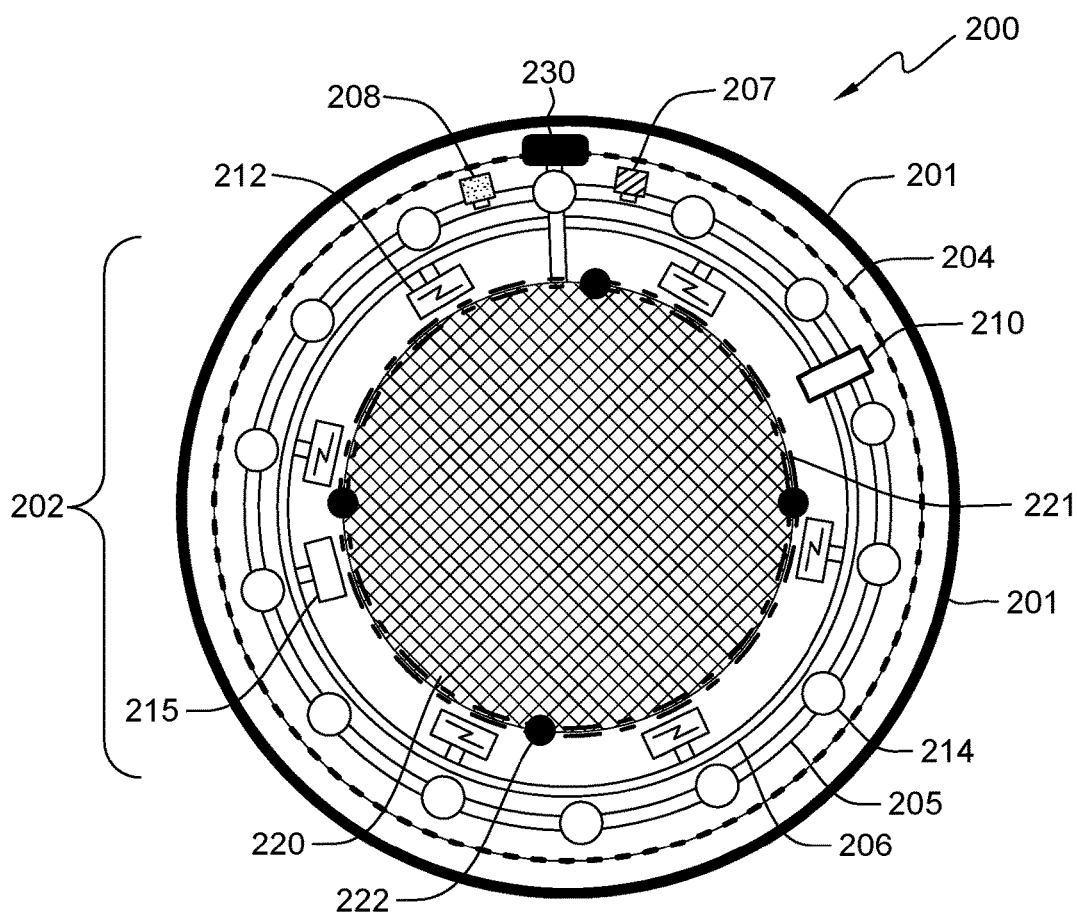
FIG. 2A is a top-down perspective view of a smart contact lens that includes ultrasonics, in accordance with an embodiment of the present invention.
Figure 2B:
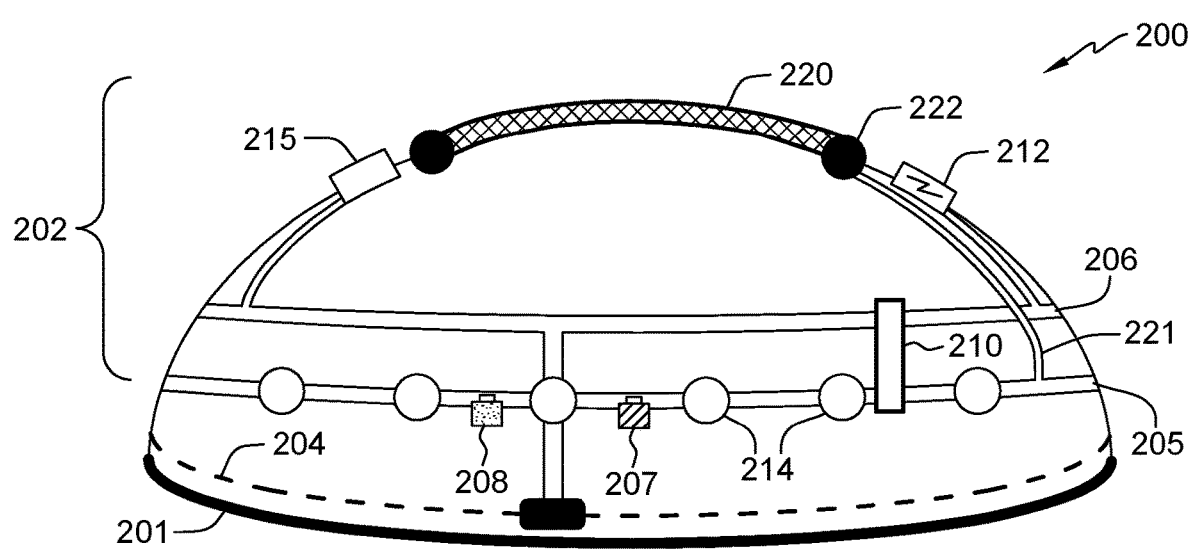
FIG. 2B is a side perspective view of a smart contact lens that includes ultrasonics, in accordance with an embodiment of the present invention.

Each smart contact of smart contact lenses 200 also include a plurality of components and other features described in further detail with respect to FIG. 2A and FIG. 2B. In an embodiment, smart contact lenses 200 includes monitoring and control program 300 implemented as firmware (not shown). In some embodiments, smart contact lenses 200 also include various aspects of smart contact program 400 implemented as firmware to enable smart contact lenses 200 to operate independent of mobile device 110, such as determining control data values. A smart contact of smart contact lenses 200 may include components, as depicted and described in further detail with respect to FIG. 5, in accordance with embodiments of the present invention.

Monitoring and control program 300 is a program that utilizes various features and elements of smart contact lenses 200 to adjust smart contact lenses 200 in response to detecting a change to the fluid film thickness and/or index of refraction of the film of fluid over a smart contact of smart contact lenses 200, which affects the vision of a user wearing smart contact lenses 200. In some embodiments, monitoring and control program 300 pre-emptively activates one or more aspects of smart contact lenses 200 based on a prediction that additional fluid (e.g., tears) will be produced and affect the vision of a user, such as the user participating in a particular activity or inferring a change to an emotional state of the user that will produce tears.

One aspect of monitoring and control program 300 determines various values related to a film of fluid over a dictated area of an instance of smart contacts 200, such as thickness and uniformity. In some instances, monitoring and control program 300 can also determine, in near real time, a focal length change within an eye of the user wearing a smart contact of smart contact lenses 200. Some aspects of monitoring and control program 300 interface with smart contact program 400 to determine and obtain control data to a respective smart contacts. Control data may include frequency and power values to apply among respective ultrasonic transducers to produce a film of fluid over the lens portion of a smart contact that has a fluid film thickness uniform within a threshold value. Other aspects of monitoring and control program 300 interface with smart contact program 400 to determine and obtain control data to electrically manipulate the electroactive lens portions of a respective smart contact to restore clear vision to the user. Another aspect of monitoring and control program 300 determines whether to utilize external power source 120 to recharge and/or supply additional operational power (i.e., energy) to smart contact lenses 200.

Network 140 can be, for example, a local area network (LAN), a telecommunications network (e.g., a portion of a cellular network), a wireless local area network (WLAN), such as an intranet, a wide area network (WAN), such as the Internet, or any combination of the previous and can include wired, wireless, or fiber optic connections. In general, network 140 can be any combination of connections and protocols that will support communications between mobile device 110, smart contact lenses 200 and/or external power source 120, in accordance with embodiments of the present invention. In various embodiments, network 140 operates locally via wired, wireless, or optical connections and can be any combination of connections and protocols (e.g., personal area network (PAN), Bluetooth®, near field communication (NFC), laser, infrared, ultrasonic).

FIGS. 2A and 2B respectively show top-down and side-view perspective diagrams of a smart contact (i.e., one smart contact of smart contact lenses 200). FIG. 2A and FIG. 2B depict a plurality of components (e.g., hardware, electronics, and bio-compatible elements) of a smart contact. The smart contact 200 and the plurality of included components are not depicted to a particular physical scale. In addition, the quantity and positions of instances of a component can vary. It should be noted that FIG. 2A and FIG. 2B depict merely examples of embodiments of the present invention and should not be viewed as limiting the scope of the present invention. In an embodiment, at least FIG. 2A depicts an anterior view of smart contact 200.

In an embodiment, smart contact 200 includes one or more translucent bio-compatible layers (e.g., the contact lens substrate) (not shown) that support and/or include the plurality of components of smart contact 200. In an illustrated embodiment, the plurality of components of a smart contact, of smart contact 200, include antenna 204 (dashed line), interconnects 205 and 206, electrochemical storage 207 (diagonal fill), power converter 208 (speckle filled box), computing module 210 (long unfilled rectangle), a set of fluid sensor 212s (box including zig-zag symbol), a plurality of ultrasonic transducer 214 (unfilled circles), focus sensor 215 (unfilled box), electroactive lens 220 (diagonal hash area), inner interconnects 221 (double dashed line), a plurality of lens controller 222 (solid filled circles), and sensor array 230 (solid fill, round-cornered box).

In various embodiments, the plurality of components are positioned on or within the convex surface of the contact lens substrate of smart contact 200. Except for electroactive lens 220, the plurality of components are located as not to interfere or obstruct the vision (i.e., field of view) of the user, such as beyond the size of a dilated pupil of the wearer of smart contact 200. In some embodiments, the surface of one or more elements, such as focus sensor 215 of smart contact 200 are co-planar with the concave inner surface (not shown) of smart contact 200.

In an illustrated embodiment, element 201 of FIG. 2A represents a physical size/circumference associated with smart contact 200 (i.e., one smart contact of smart contact lenses 200). With respect to FIG. 2B, element 201 represents another physical size of smart contact 200. The diameter of smart contact 200 may be larger than the diameter of the iris of the eye (not shown) of a user. In an embodiment, with respect to FIG. 2A, an area associated with brackets 202 (i.e., the area internal to interconnects 205) indicates an active area where the thickness, uniformity, and/or index of refraction of a film of fluid are determined and modified. Similarly, with respect to FIG. 2B, brackets 202 indicate the physical area above interconnects 205 that includes and extends above the anterior of electroactive lens 220 indicating an active area where the thickness, uniformity, and/or index of refraction of a film of fluid (not shown) are at least determined, and which includes the area over the pupil of the wearer.

In an embodiment, antenna 204 is place around the outer circumference of smart contact 200 and conveys wireless signals (i.e., communications) between one or more components of smart contact 200, such a computing module 210 and mobile device 110. Antenna 204 is strategically placed to improve the capabilities of an antenna incorporated into smart contact 200, as the range of an antenna is affected by the length of the material provided for use as the antenna. In various embodiments, antenna 204 represents a structure with a greater area and length than is depicted, such as a spiral structure, a layered structure, and/or a fractal structure.

In some embodiments, antenna 204 provides at least two separate capabilities to smart contact 200, such as receiving inductive charging energy from external power source 120 in addition to providing wireless communications with mobile device 110. In the depicted example embodiment, antenna 204 is operatively coupled to at least power converter 208, computing module 210, and sensor array 230 via interconnects 205. In another embodiment, if computing module 210 does not include wireless communication capabilities, then one portion of antenna 204 is operatively coupled to a wireless communication unit (not shown), which in turn is operatively coupled to computing modules 210 via a portion of interconnects 205.

Interconnects 205 and interconnects 206 are structures that include a plurality of electrically conductive channels or wires (not shown). Some channels are utilized for respective transfers of electrical energy. In one example, one set of channels of interconnects 205 transfers electrical energy from electrochemical storage 207 to power computing module 210, while another set of channels of interconnects 205 selectively distribute modulated electrical energy among instances of ultrasonic transducer 214. In another example, another set of energy conducting channels of interconnects 205 transfer electrical energy from power converter 208 for storage (e.g., recharging) within electrochemical storage 207. Other channels of interconnects 205 and interconnects 206 communicate signals and data among components of smart contact 200, such as communicating signals from one or more instances of fluid sensor 212, focus sensor 215, sensor array 230, etc., to computing module 210 for analysis. Similarly, computing module 210 utilizes interconnects 205 to convey communication signals to antenna 204 for wireless transmission via network 140.

Electrochemical storage 207 is a battery, such as lithium ion battery that stores electrical energy, at one or more potentials, for use by various components of an instance of smart contact lenses 200 (i.e., a smart contact). Electrochemical storage 207 is recharged utilizing electrical energy received from power converter 208.

In one embodiment, power converter 208 represents a photodiode or solar cell that converts light energy into electrical energy that is used to recharge electrochemical storage 207 and/or to supply addition operational power to one or more components of smart contact 200. In another embodiment, power converter 208 represents electronics that convert electromagnetic energy (e.g., inductive power) received via antenna 204 into electrical energy that is used to recharge electrochemical storage 207 and/or utilized to supply addition operational power to one or more components of smart contact 200. In some embodiments, power converter 208 also performs voltage regulation and/or voltage amplification functions. In various embodiments, power converter 208 performs a combination of the previously discussed functions.

In an embodiment, computing module 210 is a microcontroller that includes firmware and flash memory storage (not shown) that stores and executes at least monitoring and control program 300. In addition, the flash memory of computing module 210 also store state data and various parameters, threshold values, preset values, predefined cues (e.g., physical responses), etc. Some parameters and values are determined by smart contact program 400 or another program executing within mobile device 110, such as a cognitive or ML program. Other values, setting, and/or cues may be user defined or determined by monitoring the operations of a smart contact lens, such as consumptions of power corresponding to various control values, durations of operations, a depletion or recharge rate for electrochemical storage 207, an eye-blink sequence indicating an affirmative response, a head movement indicating a negative response, etc. Computing module 210 may also include some aspects of smart contact program 400.

Computing module 210 can perform basic input/output (I/O) functions (e.g., sending digital commands/control signals, receiving digital data from one or more sensors), computational operations, and conversions of signals from components of a smart contact into values (e.g., measurements) for various calculations. For example, computing module 210 converts signals received from an instance of fluid sensor 212 into a film thickness value and/or index of refraction value. Computing module 210 utilizes interconnects 205, interconnects 206, and inner interconnects 221 to interface with the plurality of components of smart contact 200.

In various embodiments, computing module 210 includes additional capabilities, such as a wireless communication unit, a voltage monitor, driver circuits that selectively power instances of ultrasonic transduce 214 and/or instances of lens controller 222, analog-to-digital (A/D) converters for one or more sensors, etc. For example, computing module 210 may include driver circuits and/or digital-to-analog converts (DACs) that can selectively supply different voltages, frequencies, and/or waveforms to instances of ultrasonic transduce 214. Alternatively, if instances of ultrasonic transduce 214 include control circuits, then computing module 210 may selectively send signals containing control information to instances of ultrasonic transduce 214.

The set of fluid sensor 212 are arranged along a first convex surface of a smart contact proximate to electroactive lens 220. In an embodiment, the set of fluid sensors 212 are embedded within an external layer of a smart contact 200. In various embodiments, an instance of fluid sensor 212 can determine the thickness of a fluid (e.g., film or droplet) and output the thickness information to computing module 210 via at least interconnects 206. The thickness information maybe in a digital or an analog format based on the type of fluid sensor. In some embodiments, fluid sensor 212 can also determine an index of refraction for the film of fluid that covers (e.g., coats) an instance of fluid sensor 212.

The plurality of instances of ultrasonic transducer 214 are arranged along/around the convex surface of a smart contact proximate to antenna 204. In some embodiments, instances of ultrasonic transducer 214 are directly driven by electrical energy modulated and controlled by computing module 210. In other embodiments, the plurality of instances of ultrasonic transducer 214 include control circuits that utilizes electrical energy received from at least electrochemical storage 207 via one set of channels of interconnects 205 and control signals/information from computing module 210 via another set of channels of interconnects 205.

In one embodiment, plurality of instances of ultrasonic transducer 214 are utilized to generate a uniform film of fluid over at least electroactive lens 220 and up to an area related to brackets 202 based on detecting a change to a thickness of a film of fluid over at least the lens portion of smart contact 200. In another embodiment, the plurality of instances of ultrasonic transducer 214 are pre-emptively or proactively activated by monitoring and control program 300 to generate a virtual barrier or slow the flow of additional fluid onto the lens portion of smart contact 200 to reduce the effect on the visual acuity of the wearer of smart contact lenses 200.

In an embodiment, focus sensor 215 faces the concave inner surface of smart contact 200 and monitors the focus of an image or a target marker (not shown) on the retina (not shown) of the eye of the user (i.e., a wearer of smart contact lenses 200). The target marker produces by focus sensor 215 is not perceived by the vision of the user, such as an infrared dot and may operate on a periodic basis or activate as instructed by monitoring and control program 300. In some embodiments, focus sensor 215 is utilized to determine when clear vision is restored to the user (i.e., the wearer of smart contact lenses 200). In other embodiments, focus sensor 215 provides a coarse control of electroactive lens 220 by computing module 210 and monitoring and control program 300 until other control data is received from mobile device 110.

Electroactive lens 220 may be a single layer, a stack of layers, or a matrix of one or more clear or semi-transparent electroactive material that acts as a lens and can change one or more physical characteristics, such as vary the curvature and/or change index of refraction to modify the focus of smart contact 200 in response to electrical signals applied via one or more instances of lens controller 222. In one embodiment, electroactive lens 220 is constructed of one or more films of graphene interleaved among other polymers. In another embodiment, electroactive lens 220 is based on one or more clear electroactive polymers. In an embodiment, electroactive lens 220 is based on a combination graphene and other electroactive materials.

In the depicted example embodiment, electroactive lens 220 is depicted as a circular structure with a convex anterior surface and one concave surface, located in the central portion of smart contact 200. In some embodiments, the structure of electroactive lens 220 can be a different cross-section shape, such as biconvex or plano-convex based on the visual requirements of the wearer of smart contact 200. In addition, in various embodiments the size of electroactive lens 220 is equal to or greater that the size of a dilated pupil of the wearer of a smart contact. In other embodiments, electroactive lens 220 can be driven into a less circular structure (e.g., an oval) and/or to include thickness variations based on electrical signals or changes to electrical potentials applied via one or more instances of lens controller 222 to compensate for localized differences in the thickness of a fluid over a smart contact 200.

Inner interconnects 221 operatively couple the plurality of instances of lens controller 222 with interconnects 205, interconnects 206, and at least computing module 210 and electrochemical storage 207. In an embodiment, inner interconnects 221 is a multi-channel structure similar to interconnects 205, which provides electrical energy and control signals to a plurality of instances lens controller 222 arranged around electroactive lens 220. In a further embodiment, the structure of inner interconnects 221 also includes features utilize to determine the curvature and shape of electroactive lens 220, such as strain-gage structure, variable resistance elements, etc.

In an embodiment, instances lens controller 222 are arranged around the circumference of electroactive lens 220. In an embodiment, instances lens controller 222 adjust the curvature and/or shape of electroactive lens 220 by applying one or more voltages to one or more portions of electroactive lens 220. In some embodiments, lens controller 222 include a DAC to convert control signals received from computing module 210 into voltages that adjust a curvature and/or shape of electroactive lens 220. In other embodiments, lens controller 222 amplifies an analog signal received from computing module 210 to adjust a curvature of electroactive lens 220 to restore clear vision to the wearer of smart contact lenses 200.

In the illustrative example, sensor array 230 is operatively couple to electrochemical storage 207 and computing module 210 via a interconnects 205. In some embodiments, sensor array 230 is positioned further inboard of antenna 204 along interconnects 205.

In an embodiment, sensor array 230 is an array of sensors to determine other related data and contextual information associated with the user in response to activating one or more features of smart contact lenses 200, such as environmental information (e.g., temperature, an air flow speed into an eye of user, pressure, fume/chemical detection, an excessive illumination level); motions corresponding to the head of the user; audible sounds produced by the user during an emotional state, such as laughter, sobbing, choking, etc. In one example, sensor array 230 can detect irritating fumes that cause tears, such as from cut onions or certain spices. In another example, sensor array 230 can also detect occurrences of eye blinking by the user.

Figure 3:
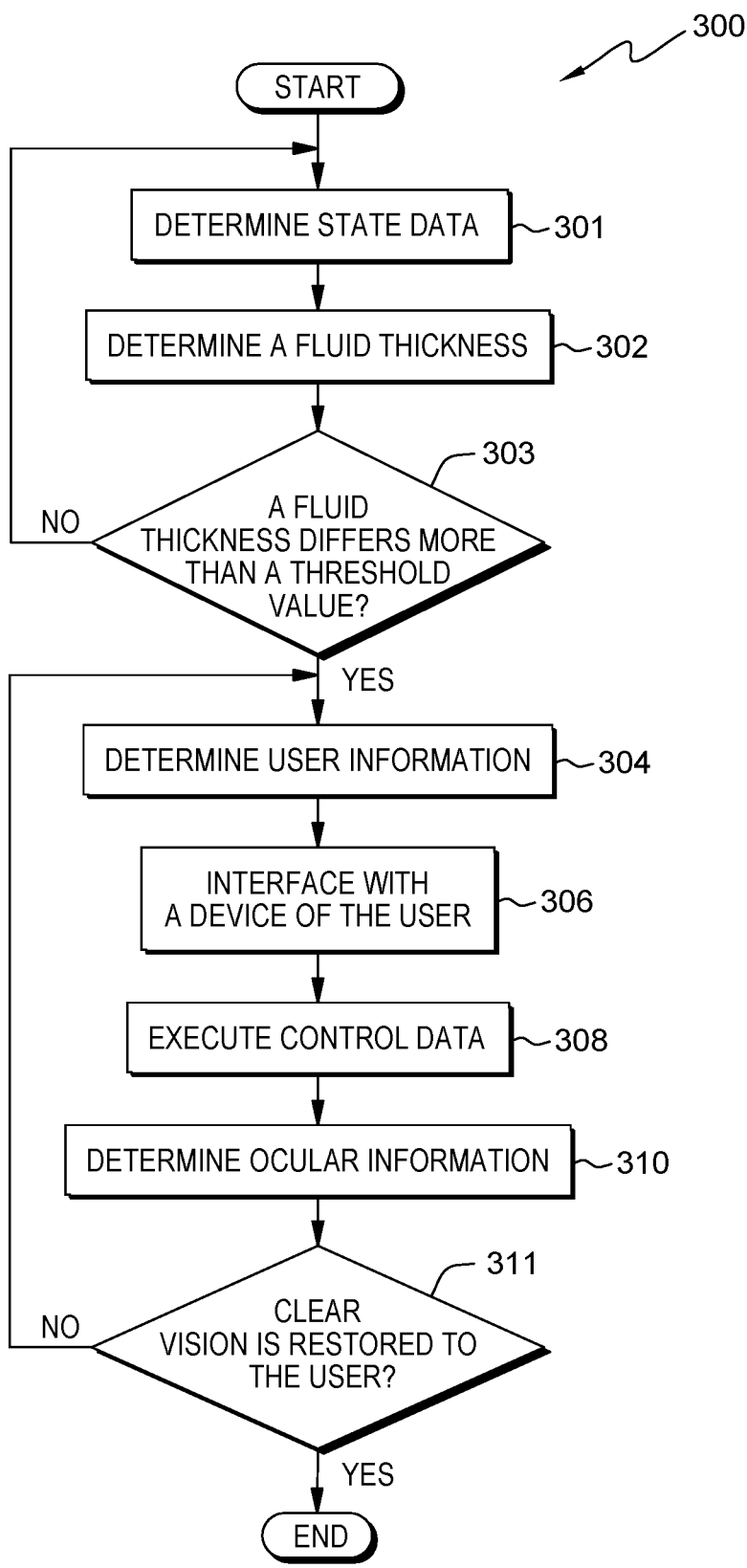
FIG. 3 depicts a flowchart of steps of a monitoring and control program, in accordance with an embodiment of the present invention.

FIG. 3 is a flowchart depicting operational steps for monitoring and control program 300, a program for obtaining information from one or more components of a smart contact of smart contact lenses 200, interfacing with smart contact program 400 executing within mobile device 110, and controlling one or more aspects of smart contact lenses 200, in accordance with embodiments of the present invention. In various embodiments, an instance of monitoring and control program 300 executes within computing module 210 corresponding to each smart contact that the user wears. In addition, monitoring and control program 300 can signal external power source 120 to recharge and/or supply additional power to smart contact lenses 200.

In some embodiments, monitoring and control program 300 holds or suspends the operation of one for more aspects (e.g., features and/or functions) of smart contact lenses 200 in response to detecting an eye blink of the user. In other embodiments, monitoring and control program 300 is quiesced until activated by computing module 210, such as detecting a fluid film thickness change among the plurality of instances of fluid sensor 212, or in response to detecting a change based on information received from sensor array 230.

In step 301, monitoring and control program 300 determines state data. In one embodiment, monitoring and control program 300 determines state data for one or more aspects of a respective smart contact of smart contact lenses 200 that a user wears. In one example, state data includes a current level of power within electrochemical storage 207, the components of the respective smart contact that computing module 210 is controlling and/or driving at a given instance of time, a set of control values utilized to by computing module 210 to control a component, etc. In another example, state data may also include environmental and/or contextual data (described above with respect to sensor array 230) determined by sensor array 230 with respect to the user wearing smart contact lenses 200, etc.

In some embodiments, a respective instance of monitoring and control program 300 determines that electrochemical storage 207 of the respective smart contact needs recharging. Recharging of a respective smart contact of smart contact lenses 200 can occur in parallel with one or more steps discussed below.

In step 302, monitoring and control program 300 determines a fluid thickness. In an embodiment, monitoring and control program 300 determines a fluid thickness of a film or droplet coating each instance of fluid sensor 212 for a smart contact. In some embodiments, monitoring and control program 300 also determines an index of refractions associated with the film of fluid or droplet that coats each instance of fluid sensor 212. In various embodiments, monitoring and control program 300 determines other values associated with a film of fluid, such as an average thickness and variation values among the fluid thickness measurements.

In decision step 303, monitoring and control program 300 determines whether a fluid thickness differs more than a threshold value. Monitoring and control program 300 utilizes threshold values and/or preset value stored within flash memory of a respective computing module 210 for various determinations. In one embodiment, monitoring and control program 300 determines that the variation among the fluid thickness values differs more than (i.e., exceeds) a first threshold value (e.g., a uniformity threshold). In another embodiment, monitoring and control program 300 determines that the average fluid thickness value differs more than a second threshold value (e.g., excessive fluid). In an embodiment, monitoring and control program 300 determines that the index of refraction values of a fluid covering one or more instances of fluid sensor 212 differs from the index of refraction that the curvature of electroactive lens 220 is based on for correcting the vision of the user and differs more than a third threshold value. In some embodiments, monitoring and control program 300 determines that two or more threshold values differ from a setting or preset value stored within a respective computing module 210. In a further embodiment, if monitoring and control program 300 determines that data obtained from sensor array 230 indicates a potential for the eyes of the user to tear, then monitoring and control program 300 skips decision step 303 and determines user information in step 304.

Responsive to determining that a fluid thickness differs does not differ more than a threshold value a threshold value (No branch, decision step 303), monitoring and control program 300 loops to state data of a respective smart contact (step 301). In an embodiment, if monitoring and control program 300 determines that at least one fluid measurement related value does not differ by more than a respective threshold value (No branch, decision step 303), then monitoring and control program 300 loops to state data of a respective smart contact (step 301). In some embodiments, to conserver power monitoring and control program 300 delays looping to step 301 based on a preset duration stored within computing module 210.

Referring to decision step 303, responsive to determining that a fluid thickness is greater than a threshold value (Yes branch, decision step 303), monitoring and control program 300 determines user information (step 304). In various embodiments responsive to determining that that at least one measurement value related fluid thickness differs by more than a respective threshold value (Yes branch, decision step 303), monitoring and control program 300 determines user information (step 304).

In step 304, monitoring and control program 300 determines user information. Monitoring and control program 300 may determine user information from a combination of sources. In one embodiment, monitoring and control program 300 determines user information based on environmental and/or contextual data determined by sensor array 230 with respect to the user wearing smart contact lenses 200. In one example, monitoring and control program 300 determines the environmental factors that the user is exposed to. In another example, monitoring and control program 300 determines one or more activities that the user engages in based on data obtained from at least sensor array 230. In some embodiments, monitoring and control program 300 infers an emotional state of the user based on the determined contextual data and/or other measurements determined by sensor array 230.

In other embodiments, monitoring and control program 300 interfaces with mobile device 110 to determine user information, such as accessing user activity data 112. In various embodiments, monitoring and control program 300 can further determine the potential of generating tears or a change to a film of fluid over smart contact lenses 200 based on at least the determined user information.

In step 306, monitoring and control program 300 interfaces with a device of the user. In one embodiment, a respective instance of monitoring and control program 300 interfaces with mobile device 110 to communicate and exchange data and information with smart contact program 400 for a respective smart contact. For example, monitoring and control program 300 transfers state data and a plurality of measurement (i.e., sensor) data to mobile device 110 for analysis by smart contact program 400. In response, the respective instance of monitoring and control program 300 receives a set of respective control data utilized to drive and/or control various components of the respective smart contact, such as electroactive lens 220. In some scenarios, monitoring and control program 300 interfaces with mobile device 110 in response to one or more changes to a film of fluid over a smart contact. In other scenarios, monitoring and control program 300 interfaces with mobile device 110 to pre-emptively react to a situation that is predicted affect the visual acuity of the user wearing smart contact lenses 200.

In another embodiment, monitoring and control program 300 determines that smart contact lenses 200 needs recharging and instructs computing module 210 to establish wireless communications with an instance of external power source 120 using network 140. In response, external power source 120 beings recharging electrochemical storage 207 of smart contact 200 via power transmission link 130. In some embodiments, monitoring and control program 300 determines, based on control data received from mobile device 110, that electrochemical storage 207 cannot independently supply sufficient electrical energy to drive the components of a respective smart contact to dictated operational conditions. In response, monitoring and control program 300 interfaces instructs (i.e., commands) computing module 210 to establish wireless communications with an instance of external power source 120 using network 140 to supply operational power to smart contact lenses 200 via power transmission link 130.

In step 308, monitoring and control program 300 executes control data. In an embodiment, a respective instance of monitoring and control program 300 executes control data received from mobile device 110 to operate (i.e., drive) a plurality of components of a respective smart contact to restore clear vision to the wearer of smart contact lenses 200. In addition, monitoring and control program 300 may pause and/or apply differing control values in response to the user blinking, closing, or rubbing a respective eye that wears a smart contact as determined by data from sensor array 230.

In one scenario, monitoring and control program 300 instructs aspects of computing module 210 to drive or apply control data values among the plurality of instances of ultrasonic transducer 214 to produce a more uniform film of fluid over at least the portion of a smart contact that includes electroactive lens 220. Alternatively, monitoring and control program 300 instructs aspects of computing module 210 to drive or apply control data values among the plurality of instances of ultrasonic transducer 214 to proactively generate a virtual boundary to block or slow additional fluid from the lens area. In another example, monitoring and control program 300 instructs other aspects of computing module 210 to drive or apply control data values among the plurality of instances of lens controller 222 to drive electroactive lens 220 to a dictated curvature and/or shape.

In step 310, monitoring and control program 300 determines ocular information. In various embodiments, monitoring and control program 300 analyzes data from one or more sensors, such as instances of fluid sensor 212 or focus sensor 215 to determine ocular information. In one embodiment, monitoring and control program 300 determines whether the received control data produces a film of fluid over the portion of a smart contact that includes electroactive lens 220 that is uniform within a threshold value. If monitoring and control program 300 determines that the received control data does not produce a film of fluid that differs less than a threshold value, then monitoring and control program 300 interfaces with mobile device 110 to obtain another set of control data from smart contact program 400. In addition, monitoring and control program 300 can utilize sensor array 230 to determine other ocular information related to an eye of the user, such as blinking (e.g., patterns, frequencies); rubbing a closed eye; information respectively associated with a condition or activity of the user.

In another embodiment, monitoring and control program 300 also determines ocular information related to the visual clarity of the user. In one scenario, monitoring and control program 300 predicts that clear vision is restored to a respective eye of the user based on focus sensor 215 identifying an "in focus" condition of the respective retina of the user. For example, monitoring and control program 300 utilizes computing module 210, information stored in flash memory, and other components of a smart contact to determine and execute control data, such as using focus sensor 215 to provide a coarse control of electroactive lens 220. In another scenario, monitoring and control program 300 determines whether clear vision is restored to the user based on feedback obtained from the user via sensor array 230, such as a verbal response or other physical cues (e.g., a predefined sequence of eye blinks, a predefined set of head motions) indicating an affirmative or a negative response from the user.

In decision step 311, monitoring and control program 300 determines whether clear vision is restored to the user. In one embodiment, monitoring and control program 300 predicts that clear vision is restored to the user based on information determined ocular information, such as data from focus sensor 215. However, one or more actions or responses of a user can override a clear vision determination made by an instance of monitoring and control program 300. In another embodiment, monitoring and control program 300 determines that clear vision is restored to the user based on predefined affirmative user cues.

Responsive to determining that clear vision is not restored to the user (No branch, decision step 311), monitoring and control program 300 loops to step 304 to determine other user information. In some embodiments, responsive to determining that clear vision is not restored to the user (No branch, decision step 311) information monitoring and control program 300 return to step 310 as opposed to looping to step 304 to determine changes to state data that affects smart contact lenses 200.

Referring to decision step 311, responsive to determining that clear vision is restored to the user (Yes branch, decision step 311), monitoring and control program 300 terminates. In some embodiments, monitoring and control program 300 quiesces until a sensor of smart contact lenses 200 and computing module 210 detect a change from one or more sensors, such as a fluid thickness change detected by fluid sensors 215 or environmental/contextual data determined by sensor array 230.

Figure 4:
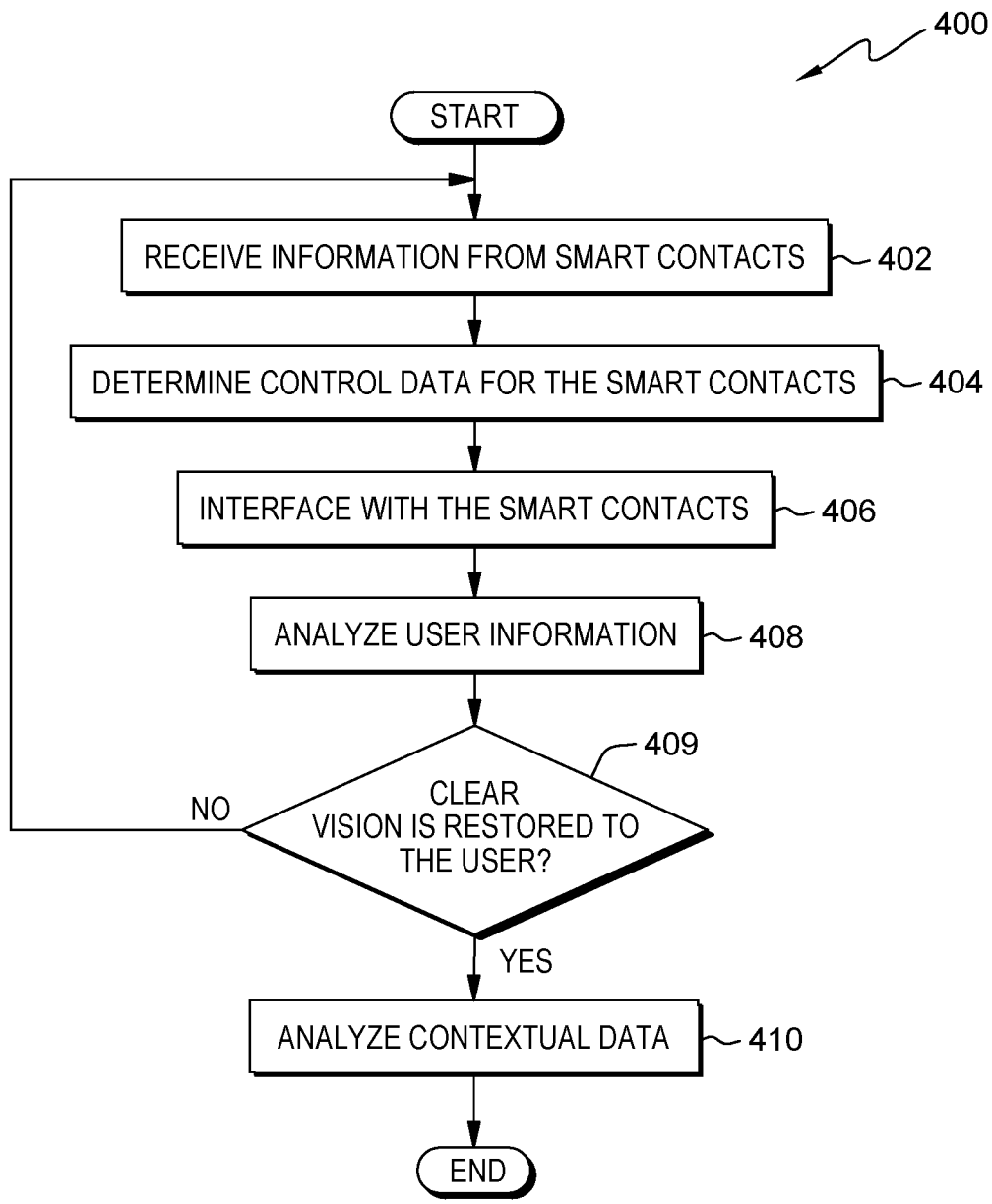
FIG. 4 depicts a flowchart of steps of a smart contact program, in accordance with an embodiment of the present invention.

FIG. 4 is a flowchart depicting operational steps for smart contact program 400, included within mobile device 110, a program for respective determining control data for one or more components of a respective smart contact of smart contact lenses 200 in response to receiving sensor information and contextual data from control and monitoring program 300 executing within a respective smart contact of smart contact lenses 200.

In step 402, smart contact program 400 receives information from smart contacts. In an embodiment, smart contact program 400 receives information from a respective smart contact of smart contact lenses 200 that the user is wearing via network 140. The received information may include but is not limited to state data, environmental and/or contextual data determined by sensors 230, occurrences of eye blinking, a current curvature and/or shape of electroactive lens 220, and information associated with other components of a respective smart contact, information related to a film of fluid (e.g., thickness, uniformity, index of refraction) covering a smart contact, etc. Smart contact program 400 may also receive environmental data, contextual data, and other activity data and information obtained from sensors 230 within activity data 112.

In other embodiments, smart contact program 400 can also obtain data and information lacking from information received from smart contact lenses 200 utilizing mobile device 110 of the user. For example, if sensor array 230 does not include a microphone or other sound pickup or other another feature to determine an affirmative or negative response from the wearer (i.e., user) of smart contact lenses 200, then smart contact program 400 utilizes features of mobile device 110 to determine a user response. Smart contact program 400 can store state and other data associated with smart contact lenses 200 within smart contact data 114.

In step 404, smart contact program 400 determines control data for the smart contacts. In an embodiment, smart contact program 400 determines respective sets of control data values for smart contact lenses 200 worn by the user. Smart contact program 400 may utilize historic control data values stored within smart contact data 114 to determine initial values for one or more control data values. Smart contact program 400 can utilize current state data and control values received from smart contact lenses 200 and historic control data values to determine a respective set of control data values for a respective smart contact. Data within user activity data 112 may affect one or more determinations of Smart contact program 400. In various embodiments, smart contact program 400 utilizes a double lens system calculation to determine the curvature of electroactive lens 220 needed to restore visual clarity of the user based on the current thickness of the film of fluid and/or the index of refraction of the film of fluid over a respective smart contact.

In some embodiments, smart contact program 400 iteratively determines various sets of control data values while interfacing and exchanging information and data with a respective instances of control and monitoring program 300 executing within a smart contact of smart contact lenses 200 for a period of time and/or until one or more results are achieved. In one example, smart contact program 400 iteratively determines various frequency values, power values, and/or waveforms to apply to respective instances of ultrasonic transducer 214 until the data values from a set of instances of fluid sensor 212 indicate that the film of fluid covering smart contact lenses 200 has achieved a thickness that is uniform within a given threshold. In another example, responsive to predicting a situation that can cause the eyes of the user to generate tears, smart contact program 400 determines one or more respective sets of control data to generate a virtual boundary (e.g., soundwave barrier) that stops or slow a change to the thickness of a film of fluid over a respective smart contact over the pupil of an eye of the user.

In step 406, smart contact program 400 interfaces with the smart contacts. Smart contact program 400 utilizes network 140 to wirelessly interface with one or both smart contacts of smart contact lenses 200. In an embodiment, smart contact program 400 interfaces with a respective smart contact of smart contact lenses 200 to transmit a first set of control data utilized by monitoring and control program 300 to manipulate one or more components of smart contact lenses 200. In some embodiments, smart contact program 400 iteratively exchanges information and data with a respective instance of control and monitoring program 300 executing within a respective smart contact until one or results is achieved, such as forming a uniform film of fluid over smart contact lenses 200 or determining that a change to the curvature and/or shape of electroactive lens 220 portion of a respective smart contact restores clear vision to the user.

In step 408, smart contact program 400 analyzes user information. In an embodiment, smart contact program 400 analyses user information received via control and monitoring program 300. In some embodiments, smart contact program 400 utilizes one or more features of mobile device 110 to determine contextual data related to the user and the vision of the user as opposed to utilizing data from sensor array 230 if smart contacts lenses 200 includes sensor array 230. For example, smart contact program 400 utilizes at least a camera and/or a microphone of mobile device 110 to identify cues related to affirmative or negative response associated with restoring clear vision to the user of smart contact lenses 200. In addition, smart contact program 400 utilizes other features or programs of mobile device 110 to determine the situation, activity, and/or emotional state of the user that generates additional fluid in the eyes of the user.

In decision step 409, smart contact program 400 determines whether clear vision is restored to the user. In one embodiment, smart contact program 400 determines that clear vision is not restored to a respective eye of the user based on feedback obtained from control and monitoring program 300. In another embodiment, smart contact program 400 determines that clear vision is not restored to a respective eye of the user based on analyzing feedback or negative responses of the user received via one or more features of mobile device 110. In other embodiments, smart contact program 400 determines that clear vision is not restored to a respective eye of the user based on other user actions, such as head shaking, rapid eye blinking, rubbing a closed eye, etc.

Responsive to determining that clear vision is not restored to the user (No branch, decision step 409), smart contact program 400 loops to step 402 to receive additional information from smart contact lenses 200.

Referring to decision step 409, responsive to determining that clear vision is restored to the user (Yes branch, decision step 409), smart contact program 400 analyzes contextual information (step 410).

In step 410, smart contact program 400 analyzes contextual information. Smart contact program 400 may utilize cognitive and/or ML programs (e.g., performs self-learning) to analyze the contextual information and other information within user activity data 122 to generate various predictions related to identifying situations and/or conditions that produce occurrences of fluid thickness changes over a smart contact that affects the vision of the user. In addition, smart contact program 400 may further associated an amount of fluid film thickness change or the generation of tears based on an identified situation and/or condition. In one embodiment, smart contact program 400 analyzes contextual information to determine the physical cause of a change to the thickness or uniformity of a film of fluid over smart contacts 200, such as the physical activity the user was engaged in that affected the fluid thickness over a respective smart contact. In another embodiment, smart contact program 400 analyzes contextual information to determine an emotional cause of a change to the thickness or uniformity of a film of fluid over smart contacts 200.

In various embodiments, smart contact program 400 updates smart contact data 114 with the determined information and/or prediction and related triggering conditions. In addition, smart contact program 400 can upload information and conditions for storage within the flash memory of respective computing module 210 related to predicting (e.g., anticipating) fluid thickness changes that affect the vision of the wearer of smart contact lenses 200. Thus, enabling control and monitoring program 300 to predict/anticipate an occurrence of a fluid thickness change and initiated a pre-emptive or proactive response.

Figure 5:
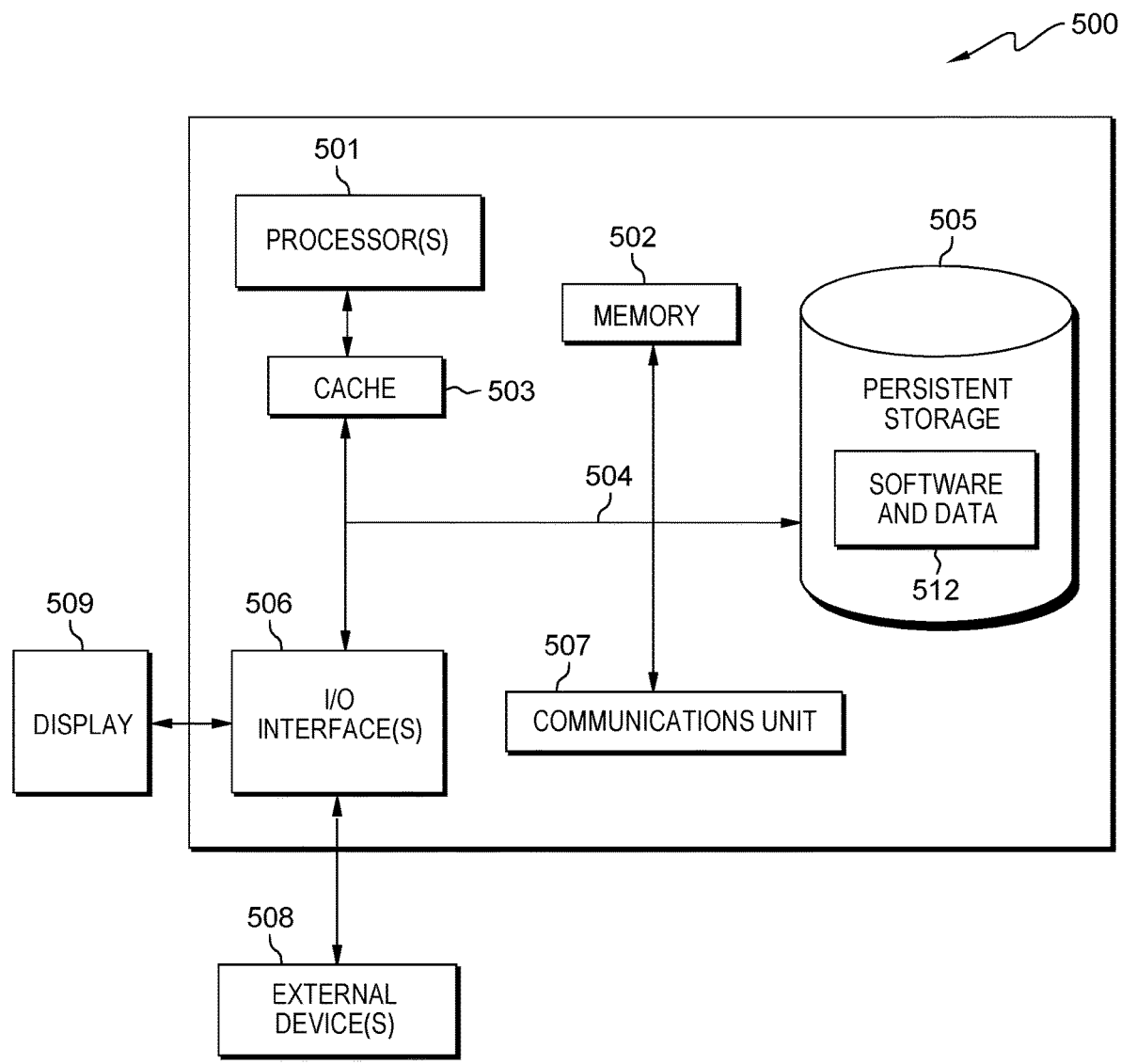
FIG. 5 is a block diagram of components of a computer, in accordance with an embodiment of the present invention.

FIG. 5 depicts computer system 500, which is representative mobile device 110 and one or more aspects of smart contact lenses 200. Computer system 500 may also represent an aspect of an instance of external power source 120. Computer system 500 is an example of a system that includes software and data 512. Computer system 500 includes processor(s) 501, cache 503, memory 502, persistent storage 505, communications unit 507, input/output (I/O) interface(s) 506, and communications fabric 504. Communications fabric 504 provides communications between cache 503, memory 502, persistent storage 505, communications unit 507, and input/output (I/O) interface(s) 506. Communications fabric 504 can be implemented with any architecture designed for passing data and/or control information between processors (such as microprocessors, communications and network processors, etc.), system memory, peripheral devices, and any other hardware components within a system. For example, communications fabric 504 can be implemented with one or more buses or a crossbar switch.

Memory 502 and persistent storage 505 are computer readable storage media. In this embodiment, memory 502 includes random-access memory (RAM). In general, memory 502 can include any suitable volatile or non-volatile computer readable storage media. Cache 503 is a fast memory that enhances the performance of processor(s) 501 by holding recently accessed data, and data near recently accessed data, from memory 502.

Program instructions and data used to practice embodiments of the present invention may be stored in persistent storage 505 and in memory 502 for execution by one or more of the respective processor(s) 501 via cache 503. In an embodiment, persistent storage 505 includes a magnetic hard disk drive. Alternatively, or in addition to a magnetic hard disk drive, persistent storage 505 can include a solid-state hard drive, a semiconductor storage device, a read-only memory (ROM), an erasable programmable read-only memory (EPROM), a flash memory, or any other computer readable storage media that is capable of storing program instructions or digital information.

The media used by persistent storage 505 may also be removable. For example, a removable hard drive may be used for persistent storage 505. Other examples include optical and magnetic disks, thumb drives, and smart cards that are inserted into a drive for transfer onto another computer readable storage medium that is also part of persistent storage 505. Software and data 512 are stored in persistent storage 505 for access and/or execution by one or more of the respective processor(s) 501 via cache 503 and one or more memories of memory 502. With respect to mobile device 110, software and data 512 includes user activity data 112, smart contact data 114, smart contact program 400, and other programs and data (not shown). With respect to smart contact lenses 200, software and data 512 includes monitoring and control program 300, and other data, programs, and firmware (not shown). With respect to some instances of external power source 120, software and data 512 includes data, programs, and firmware (not shown).

Communications unit 507, in these examples, provides for communications with other data processing systems or devices, including resources mobile device 110 and smart contact lenses 200. In some embodiments, smart contact lenses 200 utilizes communications unit 57 to transmit instructions to external power source 120. In these examples, communications unit 507 includes one or more network interface cards and/or wireless communication adapters. Communications unit 507 may provide communications, through the use of either or both physical and wireless communications links. Program instructions and data used to practice embodiments of the present invention may be downloaded to persistent storage 505 through communications unit 507.

I/O interface(s) 506 allows for input and output of data with other devices that may be connected to each computer system. For example, I/O interface(s) 506 may provide a connection to external device(s) 508, such as a keyboard, a keypad, a touch screen, and/or some other suitable input device. External device(s) 508 can also include portable computer readable storage media, such as, for example, thumb drives, portable optical or magnetic disks, and memory cards. Software and data used to practice embodiments of the present invention can be stored on such portable computer readable storage media and can be loaded onto persistent storage 505 via I/O interface(s) 506. I/O interface(s) 506 also connect to display 509.

Display 509 provides a mechanism to display data to a user and may be, for example, a computer monitor. Display 509 can also function as a touch screen, such as the display of a tablet computer or a smartphone. Alternatively, display 509 displays information to a user based on a projection technology, such as virtual retinal display, a virtual display, or image projector.

The programs described herein are identified based upon the application for which they are implemented in a specific embodiment of the invention. However, it should be appreciated that any particular program nomenclature herein is used merely for convenience, and thus the invention should not be limited to use solely in any specific application identified and/or implied by such nomenclature.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random-access memory (RAM), a read-only memory (ROM), an erasable programmable read-only memory (EPROM or Flash memory), a static random-access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general-purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be accomplished as one step, executed concurrently, substantially concurrently, in a partially or wholly temporally overlapping manner, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the invention. The terminology used herein was chosen to best explain the principles of the embodiment, the practical application or technical improvement over technologies found in the marketplace, or to enable others of ordinary skill in the art to understand the embodiments disclosed herein.

What is claimed is:

1. A smart contact apparatus comprising:
    a smart contact portion having at least a first convex surface, a second convex surface, and a concave surface, wherein the smart contact portion includes a translucent portion;
    a set of liquid thickness sensors embedded upon the first convex surface;
    an electrochemical storage device;
    a computing module;
    a plurality of ultrasonic transducers embedded upon the first convex surface, wherein the plurality of ultrasonic transducers determines an index of refraction of a film of fluid on the surface of an eye of a user;
    an electroactive lens structure embedded within central portion of the first convex surface above a pupil corresponding to the eye of the user; and
    a plurality of lens controllers, wherein one or more lens controllers apply electrical signals to the electroactive lens structure to change at least one physical characteristic of the electroactive lens structure based on control signals from the computing module.

2. The smart contact apparatus of claim 1, wherein the plurality of ultrasonic transducers are arranged along the outer circumference of the first convex surface.

3. The smart contact apparatus of claim 1, further comprising:
    an antenna portion affixed along the outer circumference of a translucent portion of the smart contact, the antenna portion electrically connected to a computing module, and the antenna portion enables wireless communications with a mobile computing device of the wearer of the smart contact.

4. The smart contact apparatus of claim 3, further comprising:
    the antenna portion enables receiving a wireless transmission of power from an external power source that is utilized to recharge the electrochemical storage device.

5. The smart contact apparatus of claim 3, further comprising:
    the computing module affixed between the outer circumference of the translucent lens portion and the center of the translucent lens portion, with the computing module electrically connected to the plurality of ultrasonic transducers, the antenna portion, and the set of liquid thickness sensors, and the computing module including a computer processor and memory.

6. The smart contact apparatus of claim 1, further comprising:
    a plurality of electrical connections embedded within the translucent lens portion, wherein:
    (i) the plurality of electrical connects includes at least a first set of electrical connections that distribute electrical energy among elements of the smart contact lens;
    (ii) a second set of electrical connection that communicate data from one or more sensors to the computing module;
    (iii) a third set of electrical connections the communicate control signals from the computing module among the plurality of ultrasonic transducers; and
    (iv) a fourth set of electrical connections that communicate control signals among one or more controllers of the electroactive lens structure one or more controllers of the electroactive lens structure.

7. The smart contact apparatus of claim 1, wherein the electroactive lens structure includes one or more layers of graphene.

8. The smart contact apparatus of claim 1, wherein a shape of an anterior portion of the electroactive lens corresponds to the second convex surface.

9. The smart contact apparatus of claim 1, wherein a plurality of components different from the electroactive lens structure are positioned outside the field of view of the wearer of the smart contact apparatus.

10. The smart contact apparatus of claim 1, further comprising:
at least one array of sensors is utilized to obtain environmental data and contextual information related to an activity of the user and a related situation that causes a change to the film of fluid over the smart contact apparatus.

11. A computer-implemented method to maintain visual clarity of a user wearing a smart contact, the computer-implemented method comprising:
determining, by a computing module, that a thickness value associated with a film of fluid over a smart contact worn on an eye of a user differs more than a threshold value, wherein determining that the thickness value differs includes the computing module determining an index of refraction of a film of fluid on the surface of the eye of the user;
determining, by the computing module, utilizing a double lens system calculation, a change to the shape of an electroactive lens structure included within the smart contact based on the determined thickness value associated with the film of fluid over the smart contact and one or more physical characteristic of the electroactive lens structure;
determining, by the computing module, a first set of control values based on the calculated change to the shape of the electroactive lens structure of the smart contact; and
applying, by the computing module, the first set of control values among a set of controllers operatively coupled to the electroactive lens structure that produce electrical signals, which modify at least a curvature characteristic of the electroactive lens structure.

12. The computer-implemented method of claim 11, wherein respective fluid thickness values are determined by an array of fluid thickness sensors embedded.

13. The computer-implemented method of claim 11, wherein the electroactive lens structure is based on a matrix of clear electroactive materials that includes at least one graphene layer.

14. The computer-implemented method of claim 11, further comprising:
determining, by the computing module, that a uniformity value of the film fluid over the smart contact worn on an eye of a user varies by more than a threshold value;
responsive to determining that the uniformity value of the film fluid over the smart contact varies by more than the threshold value, activating, by the computing module, one or more ultrasonic transducers of a plurality of ultrasonic transducers included on the smart contact; and
determining, by the computing module, after a predetermined duration, another thickness value associated with the film of fluid over the smart contact.

15. The computer-implemented method of claim 11, further comprising:
determining, by the computer module, that an electrochemical storage device of the smart contact lacks sufficient electrical energy to operate the smart contact based on one or more sets of control values;
responsive to determining that an electrochemical storage device of the smart contact lacks sufficient electrical energy to operate the smart contact based on one or more sets of control values, establishing, by the computing module, wireless communications with an external power source; and
transmitting, by the computing module, instructions to the external power source to wirelessly supply power to the smart contact.

\* \* \* \* \*